(12) United States Patent
Holtkamp, Sr.

(10) Patent No.: US 7,985,905 B2
(45) Date of Patent: *Jul. 26, 2011

(54) MULTIFLORESCENCE TRAIT IN AFRICAN VIOLETS

(75) Inventor: Reinhold Holtkamp, Sr., Nashville, TN (US)

(73) Assignee: International Plant Breeding AG, Liebefeld (CH)

( * ) Notice: Subject to any disclaimer, the term of this patent is extended or adjusted under 35 U.S.C. 154(b) by 1163 days.

This patent is subject to a terminal disclaimer.

(21) Appl. No.: 10/046,968

(22) Filed: Jan. 17, 2002

(65) Prior Publication Data

US 2003/0135899 P1    Jul. 17, 2003

(51) Int. Cl.
*A01H 5/00*    (2006.01)
(52) U.S. Cl. ........................................... 800/323
(58) Field of Classification Search ............. 800/260, 800/270, 276, 295, 298, 323; Plt./264, 265, Plt./266, 267, 268, 269, 270, 271
See application file for complete search history.

(56) References Cited

U.S. PATENT DOCUMENTS

| PP4,550 P | | 6/1980 | Holtkamp | |
|---|---|---|---|---|
| PP6,109 P | * | 2/1988 | Holtkamp, Sr. | Plt./266 |
| PP6,525 P | | 1/1989 | Holtkamp, Sr. | |
| PP6,575 P | * | 1/1989 | Holtkamp, Sr. | Plt./267 |
| PP13,786 P2 | * | 5/2003 | Holtkamp, Sr. | Plt./270 |
| PP13,789 P2 | * | 5/2003 | Holtkamp, Sr. | Plt./270 |
| PP13,818 P2 | * | 5/2003 | Holtkamp, Sr. | Plt./270 |
| PP13,842 P2 | * | 5/2003 | Holtkamp, Sr. | Plt./270 |

FOREIGN PATENT DOCUMENTS

CA    2416613 A1 *    7/2003

OTHER PUBLICATIONS

Anonymous. Ever Floris African Violet—The NEWEST series by Optimara http://www.selectivegardenercom/cgi-shl/$Webdbc.exe/model/nextid/htx/&/selective/everfloris.htx?x_cartid=usl7phOsUwpCaL15oY4Yfz8x.*
EverFloris The New Evolution of Space Violets http://www.optimara.com/everfloris.html.*
Marmor MS. Martin CE. "Effects of exposure in space on tomato seeds: Photosynthesis, biomass, and water relations of well-watered and drought-stressed plants". Photoshynthetica, 1998 V35, N4 p. 589-596.*
Raven et al. Biology of Plants, 5th ed. Worth Publishers, 1992 p. 134-135.*
Hartl, Daniel L. Genetics, $3^{Rd}$ ed. Jones and Bartlett Publishers, 1994, pp. 474-75.*
van Harten, A. M. Mutation Breeding, pp. 111-137, 1998.*

(Continued)

*Primary Examiner* — Wendy C. Haas
(74) *Attorney, Agent, or Firm* — Foley & Lardner LLP

(57) ABSTRACT

African Violet plants exhibiting the multiflorescence trait with at least one leaf axil that produces two or more flower stems are provided. African Violet plants carrying the multiflorescence trait bloom continuously. The multiflorescence trait has been successfully bred into diverse African Violet plants. The multiflorescence trait can be combined with many desirable traits including different flower colors, leaf colors and growth habit, to produce a wide variety of unique cultivars.

9 Claims, 10 Drawing Sheets
(3 of 10 Drawing Sheet(s) Filed in Color)

OTHER PUBLICATIONS

Optimara Field Guide: Space Violets date unknown accessed Jul. 25, 2008 available at: http://www.optimara.com/optimarafieldguide/spaceviolets.html.*

Optimara Violet Glossary: Sol-Sta, pp. 1 and 2, date unknown, accessed Jul. 25, 2008 available at: http://www.optimara.com/optimaraglossary/sol-sta.html.*

Optimara Field Guide: Atlanta. Date unknown, accessed Jul. 25, 2008. availalable at: http://www.optimara.com/optimara fieldguide/varietiesa-l/atlanta.html.*

Optimara Field Guide: Annie. Date unknown, accessed Jul. 25, 2008. available at: http://www.optimara.com/optimarafieldsguide/varietiesa-l/annie.html.*

Anonymous. Ever Floris African Violet—The NEWEST series by Optimara https://www.selectivegarderener.com/cgi-shl/SWebdbc.exe/model/nextid/htx/&/selective/everfloris.htx?x_cartid=usl7phOsUwpCaLl5oY4Ytz8x accessed May 22, 2003.*

Theodore James, Jr.: How to Select and Grow African Violets and Other Gesneriads, pp. 40-43 (HP Books, 1983).

* cited by examiner

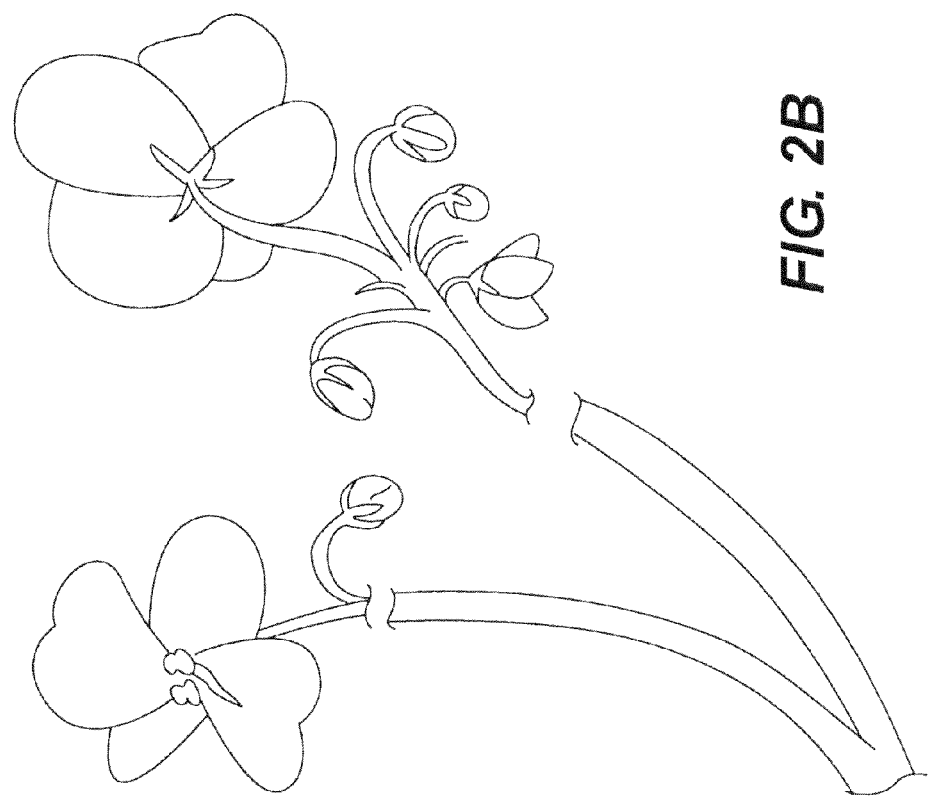

MULTIFLORESCENCE TRAIT IN AFRICAN VIOLETS

FIELD OF THE INVENTION

The present invention relates to a new, distinct and stable trait of African Violets hereinafter referred to as the "multiflorescence" trait. Multiflorescence means that a leaf node may have at least 2 flower stems. The multiflorescence trait includes selections with 3, 4, 5, or more flower stems at a leaf node. Because the second and subsequent generations of flower stems form on plants carrying the multiflorescence trait, these plants continuously bloom. As the first generation flower stem wilts, the second generation flower stem is already producing more flowers. Under ideal growing conditions, with adequate fertilization, the number of flower stems per leaf node increases, as the plant ages.

BACKGROUND OF THE INVENTION

African Violets are grown for sale as domestic house plants. They are one of the most popular and widely enjoyed house plants in the United States and around the world. New cultivars are developed through controlled breeding programs leading to desirable and stable characteristics. Among the characteristics commercial breeders strive to develop in new cultivars through traditional breeding are attractive flower colors, profuse flowering and a long flowering period, among others.

Thus far, traditional breeding techniques have failed to produce African Violet cultivars that stably produce more than one flower stem from one leaf node or leaf axil. The leaf node or leaf axil refer to the place where a leaf joins the main axis of the plant. African Violet plants produce a flower stem that grows from the leaf node or leaf axil.

The profusion and duration of flowering stems on known cultivars is limited. Attempts have been made to increase the number of flowers produced by African Violet cultivars through increasing the number of leaf nodes. However, the uniform plant habit is lost as the number of leaf nodes increases.

There is a need therefore for new strategies for producing African Violet plants with increased numbers of flower stems, larger numbers of flowers and more continuous flowering habit.

SUMMARY OF THE INVENTION

The instant invention provides African Violet plant selections that have 2, 3, 4, 5 or more flower stems at a leaf axil. African Violet plants that have 2, 3, 4, 5 or more flower stems at each leaf axil carry the multiflorescence trait. Also provided is a method of producing new African Violet selections that produce 2, 3, 4, 5 or more flowers stems at a leaf axil by crossing a first plant selection carrying the multiflorescence trait with a second plant selection that does not carry the multiflorescence trait but exhibits a second trait of interest, and selecting progeny that exhibits multiflorescence and the second trait of interest.

The instant invention also provides an African Violet plant comprising at least one leaf axil that produces more than one flower stem. The African Violet plant may have a leaf axil that produces at least 3, 4, or 5 flower stems.

Also provided is an African Violet plant wherein the plant is produced from seeds having ATCC deposit Accession No. PTA-3982 and comprises at least one leaf axil that produces more than one flower stem.

The instant invention provides a method of producing an African Violet plant having at least one leaf axil with more than one flower stem and a second desirable trait, the method comprising the steps of crossing, as the male or female parent, a first African Violet plant that has at least one leaf axil with more than one flower stem, with a second African Violet plant having a second desirable trait but only 1 flower stem on any leaf axil, and selecting progeny that have at least one leaf axil with more than one flower stem and the second desirable trait. The second desirable trait is selected may be flower color, leaf color, disease resistance, leaf size, growth habit, among others.

The instant invention also provides a method of increasing the number of flower stems per leaf axil in a African Violet plant comprising the steps of crossing a first plant that exhibits the multiflorescence trait with a second plant that exhibits the multiflorescence trait and selecting progeny from the cross that produce more flower stems per leaf axil than either parent.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2B shows a hand-drawn sketch of the multiflorescence characteristic.

DETAILED DESCRIPTION OF THE PREFERRED EMBODIMENTS

Figure 1:
FIG. 1 shows the cultivar 'SB 4-2 Muflo' which has the multiflorescence trait and was the preferred breeding stock for four new cultivars exhibiting the multiflorescence trait. The photograph shows three flower stems, all coming out of one single leaf axil, each one in a different stage of development. The first flower stems carries flowers that have just wilted. The second flower stem is in a mature stage with some open flowers and others are buds. The third flower stem carries only buds.
Figure 2A:
FIG. 2A shows a photograph of two flower stems from 'SB4-2 Muflo' attached together as found in one leaf axil.
Figure 3A:
FIG. 3A shows a photograph of the African Violet cultivar 'Molokai' (U.S. Plant Patent No. PP6525) that produces one flower stem at each leaf node.
Figure 3B:
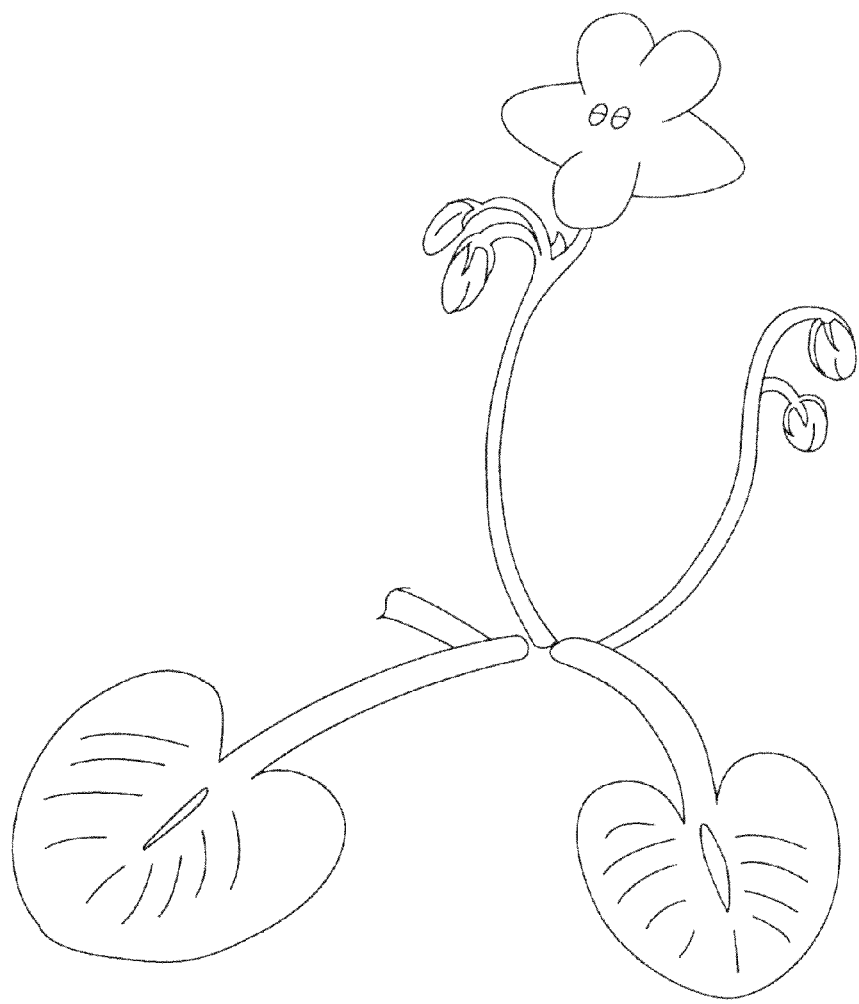
FIG. 3B shows a hand-drawn sketch of the flower stem arrangement on a typical African Violet cultivar plant that does not exhibit the multiflorescence trait.

The multiflorescence trait is firmly fixed in the breeding stock described herein and is retained through successive generations of asexual or sexual reproduction. The present invention also relates to introducing the multiflorescence trait into diverse African Violet cultivars to produce plants exhibiting the multiflorescence trait that in combination with many different characteristics such as various petal colors, leaf shapes, leaf color, among others.

The project that resulted in production of the multiflorescence trait began in April 1984. During the 1984 Space Shuttle launch, and in cooperation with the National Aeronautics & Space Administration (NASA) and the Park Seed Company, the inventor sent over 25,000 African Violet seeds into space. The seeds were incubated in a weightless environment for six years on the Long Duration Exposure Facility (LDEF). During this period the seeds were exposed to cosmic radiation and lack of gravity. The seeds were retrieved in January of 1990 and were sown in March of 1990 within a controlled research environment at the inventor's Research facility in Nashville, Tenn.

Among the interesting mutant phenotypes observed among the plants grown from these seeds was the multiflorescence trait. African Violet plants exhibiting the multiflorescence trait have at least one leaf axil with more than one flower stem. Preferably, the African Violet plant exhibiting the multiflorescence trait has more than one leaf axil that has more than one flower stem per axil. More preferably, an African Violet plant exhibiting the multiflorescence trait has a leaf axil that produces at least 2, 3, 4, or more flower stems per leaf axil.

This invention includes a breeding method for transmitting to new cultivars of African Violets the trait or characteristic of multiflorescence, and the propagative material needed to accomplish this.

The African Violet seeds from the cross of cultivars 'H 25/2" and G 68/1' were incubated on LDEF for six years. A mutant plant obtained from these seeds exhibited the multiflorescence trait and was designated 'SB 4-2 Muflo'. 'SB 4-2 Muflo' was crossed to diverse African Violet plants to introgress the multiflorescence trait Accession No. PTA-3982. Plants from the seeds produced, from the cross of 'SB 4-2 Muflo' with 'P 6/6' and deposited with the ATCC can be crossed with any African Violet plant to produce progeny that exhibit the multiflorescence trait.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

Example 1

'SB 4-2 Muflo'

'SB 4-2 Muflo' was produced from the cross of selection 'H 25/2' with 'G 68/1'. The African Violet seeds from the cross of cultivars 'H 25/2' and G 68/1' were incubated on LDEF for six years. A mutant plant obtained from these seeds exhibited the multiflorescence trait and was designated 'SB 4-2 Muflo'. Asexual reproduction of the new cultivar by leaf cuttings, as performed by the inventor in Nashville, Tenn., has demonstrated that the combination of characteristics as herein disclosed for the new cultivar are firmly fixed and retained through successive generations of asexual reproduction. Cuttings for asexual propagation can be taken at any time of the year and no special hormones or soil mixtures are used.

'SB 4-2 Muflo' has not been observed under all possible environmental conditions. The phenotype may vary significantly with variations in environment such as temperature, light intensity and day length, however, it has been determined that the multiflorescence characteristics is highly stable even with less than optimum growing conditions.

The following observations, measurements and values describe the new cultivar as grown in Nashville, Tenn. under greenhouse conditions which closely approximate those generally used in commercial practice.

The following traits have been repeatedly observed and are determined to be basic characteristics of 'SB 4-2 Muflo', which in combination distinguish this African Violet as a new and distinct cultivar: strong, upright flower stems curving slightly toward the center; small medium-blue flowers with darker center; multiflorescence trait with 2-3 flower stems per leaf axil; 13-16, or more, upright flower stems per plant, each of which carries 10-13, or more, flowers. The cultivar exhibits long-lasting, non-dropping flowers. The plant is saleable 8 to 10 weeks after potting. The cultivar exhibits vigorous and compact growth habit. Seed capsules of 'SB 4-2 Muflo' push slightly through. The cultivar has medium green, oval to heart-shaped leaves. After maturity the flowers dry off, and remain on the peduncle without becoming infected by Botrytis.

The new cultivar is most similar to cultivar 'Manitoba' as disclosed in U.S. Plant Patent No. PP4550. 'Manitoba' and 'SB 4-2 Muflo' have similar flower and leaf color. 'SB 4-2 Muflo', however, is a far superior cultivar due to the multiflorescence trait. The accompanying color photographic drawing shows a typical specimen plant of the new cultivar. The colors appearing in the photograph are as true as possible with color illustrations of this type.

In the following description, color references are made to the Royal Horticultural Society Colour Chart (RHS), except where general colors of ordinary significance are referred to. Color values were taken under natural sunlight conditions at approximately 12 p.m. in Nashville, Tenn.

Botanical Classification: *Saintpaulia ionantha*, Ramat., c.v. SB 4-2 Muflo

Parentage:
    Male parent: 'H 25/2'
    Female parent: 'G 68/1'

Propagation: The new cultivar holds its distinguishing characteristics through successive propagations by leaf cuttings.

Plant: From 9 cm to 11 cm tall when grown in pots, and 20-25 cm diameter when fully grown.
    Leaves:
        General form: Oval to heart-shaped
        Diameter: 60-70 mm wide and 75-85 mm long
        Texture: Leathery
        Aspect: Hairy, slightly serrated, slightly shiny
        Veins: Upperside: visible; underside: well pronounced, light green to purplish red, shiny.
        Color (upperside): Yellow-green RHS 147 A
        Color (underside): Greyed-green RHS 194 C
        Petiole: Strong, green with purplish brown touch, hairy.

Flowers:
  Buds: Bell-shaped, light blue and greenish, 5-7 mm just before opening.
  Sepals: Five
    Color: Green with purplish brown touch
  Calyx:
    Shape: Funnel-shaped
    Aspect: Spear-shaped, hairy
  Peduncle:
    Character: Strong upright, hairy
    Color: Purplish brown
  Individual flowers:
    Size: 32-36 mm
    Shape: Single, violet-shaped
    Color (upperside): Between Violet-Blue RHS 94 B and RHS 94 C with center being Violet-Blue RHS 93 B. Under cooler temperatures and more intensive lighting, the light blue tends to intensify.
    Color (underside): Violet RHS 88 D
    Borne: Each flower stem carries 10-13 and more flowers on strong, upright peduncles that are free standing above
    Flowering habit: Flowers 8-10 weeks after potting
  Reproductive Organs:
    Stamens: Two. Anthers: 2 composed of 4 anther cells, seed capsules push slightly through.
    Filaments: Yellowish white, 3-4 mm long
    Pollen Color: Yellow RHS 7 A
    Styles: 6-7 mm long, light blue, base of ovary light green and hairy.
  Roots: Normally developed, white when young, turning slightly brownish when older.
Disease Resistance: 'SB 4-2 Muflo' has shown very good resistance to all major violet diseases.
General Observations:
  'SB 4-2 Muflo' is an attractive cultivar due to its abundance of medium-blue flowers contrasting nicely with the bright yellow anthers. A tight flower bouquet that is free-standing and above the leaves develops after 8-10 weeks. Each of the 13-16, or more, strong flower stems carries 10-13, or more, flowers. Due to its multiflorescence characteristic, under ideal growing conditions the cultivar is never without blooms. Medium-green, heart-shaped leaves surround the flower bouquet. The flowers are long-lasting and non-dropping and the seed capsules push slightly through.

Example 2

Breeding of New Multiflorescence Cultivars

A breeding program was undertaken using 'SB 4-2 Muflo' as a breeding stock for the transfer of the multiflorescence trait into diverse genetic African Violet backgrounds to produce new and unique multiflorescence cultivars. This goal was accomplished by means of crossing 'SB 4-2 Muflo' with selected parents of the established research program. Any African Violet selection carrying the multiflorescence trait could be substituted for 'SB 4-2 Muflo' as parent material for this breeding program. 'P 40/9' for example, has been successfully used as breeding stock to produce new African Violet selections that exhibit the multiflorescence trait. African Violet plants are cultivated and crossed according to any methods well known to those working in this field such as the methods described in *How To Select and Grow African Violets and Other Gesneriads* by Theodore James, Jr (HP Books, 1983).

Figure 4:
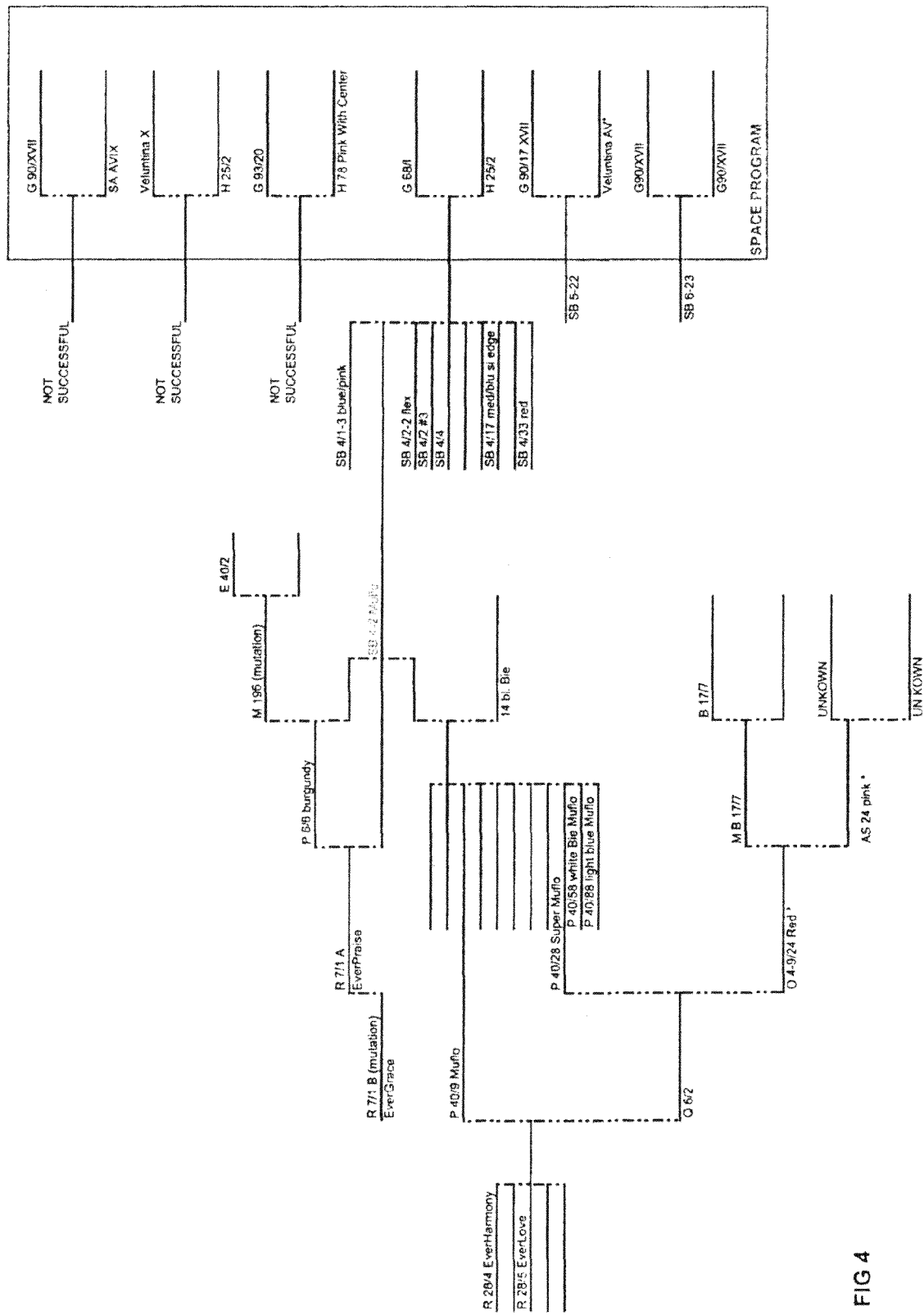
FIG. 4 shows the entire genealogy of the multiflorescence program from the seeds collected from the space program to development of the four commercial multiflorescence cultivars.

FIG. 4 shows the entire genealogy of the multiflorescence program from the seeds collected from the space program to development of the four commercial multiflorescence cultivars. The term "muflo" means the cultivar displays the multiflorescence trait. FIGS. 4 to 8 show the crosses made with 'SB 4-2 Muflo'.

'SB 4-2 Muflo' was one of about 20 phenotypes obtained from the cross between the parents 'G 68/1', a red frilled cultivar, and 'H 25/2' a cultivar exhibiting the multiflorescence trait. Of the 20 phenotypes obtained and designated 'SB' for Space Baby, all had the multiflorescence trait. Only the 7 best cultivars were selected. 'SB 4-2 Muflo' produces medium-blue flowers with a high degree of multiflorescence and was used successfully as breeding stock. Subsequently, it was crossed with non-multiflorescence cultivars and yielded new cultivars exhibiting the desired multiflorescence traits. These cultivars proved to be stable and were in turn crossed with other regular type cultivars in order to introduce other colors and characteristics into the breeding program. The multiflorescence cultivars were crossed to each other in order to increase the number of flower stems produces per leaf axil and the total number of each leaf axil per plant that produce more than one flower stem. The breeding program also included backcrossing new multiflorescence cultivars with one parent.

Figure 7:
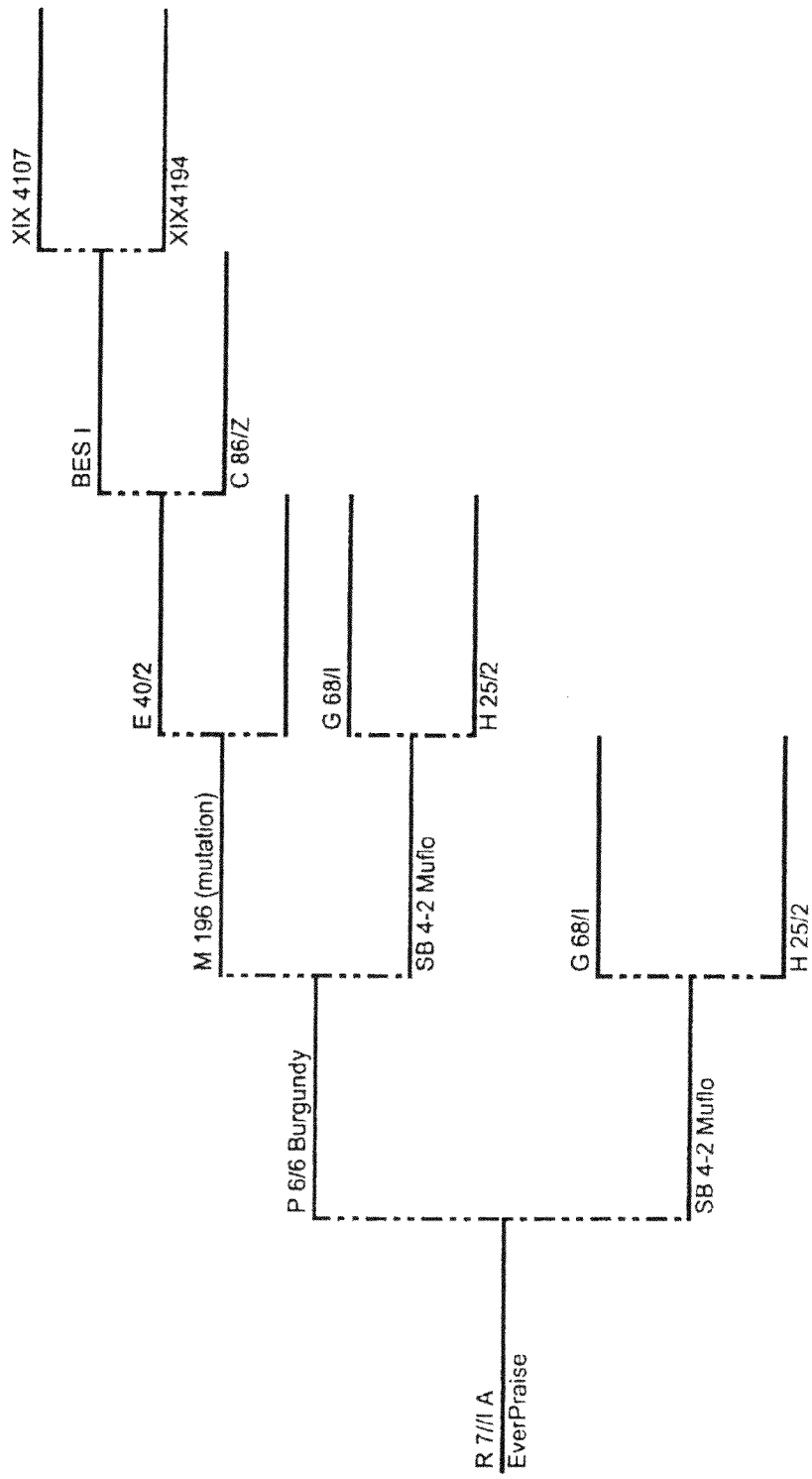
FIG. 7 shows crosses made with 'SB4-2 Muflo' and 'M-196' to produce multiflorescence cultivar 'EverPraise', which is described in U.S. Plant Patent No. 13,389, filed Jan. 17, 2002 and issued May 6, 2003, and incorporated herein by reference.
Figure 8:
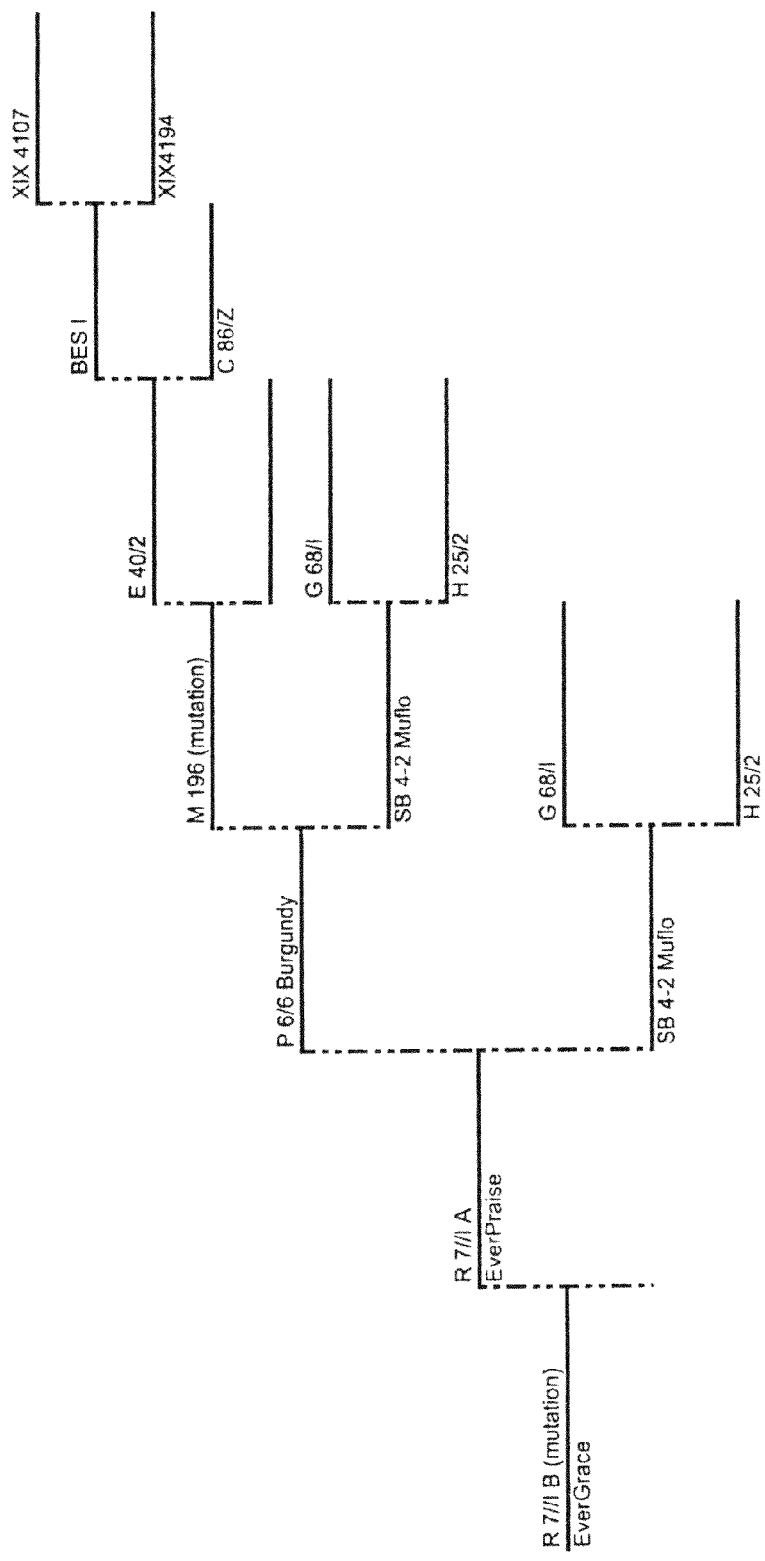
FIG. 8 shows crosses made with 'SB4-2 Muflo' and 'M-196' to produce multiflorescence cultivar 'EverGrace', which is described in U.S. Plant Patent No. 13,818, filed Jan. 17, 2002 and issued May 13, 2003, and incorporated herein by reference.

FIGS. 7 and 8 show the breeding work done with 'SB 4-2 Muflo' crossed with 'M 196' a non-multiflorescence cultivar that produces blue flowers with a white edge. This cross produced a large number of phenotypes of which 7 phenotypes were selected as the best ones. Even though there were no multiflorescence offspring achieved in this cross, one was selected because of its beautiful and distinctive green edge. 'P 6/6' produces flowers with a burgundy color and a green edge. Because of its special characteristic of having a green edge, 'P 6/6' was crossed back to 'SB 4-2 Muflo'. From this cross, 5 offspring were recorded and named 'R 7/1' to 'R 7/5'. Of the 5 phenotypes, 3 (60%) displayed the multiflorescence trait. The best selection of this cross was 'R7/1 A', that produces medium-blue flowers with frilled greenish edge which has been commercially named 'EverPraise'. Asexual reproduction of 'R7/1' eventually yielded a mutation with the same characteristics as 'R7/1 A' except for its different flower color—bi-colored white with medium blue center and edges ending with the same frilled green edge. This mutant was commercially named 'EverGrace'. Both 'EverPraise' and 'EverGrace' have proved to be stable multiflorescence cultivars through asexual reproduction.

Figure 5:
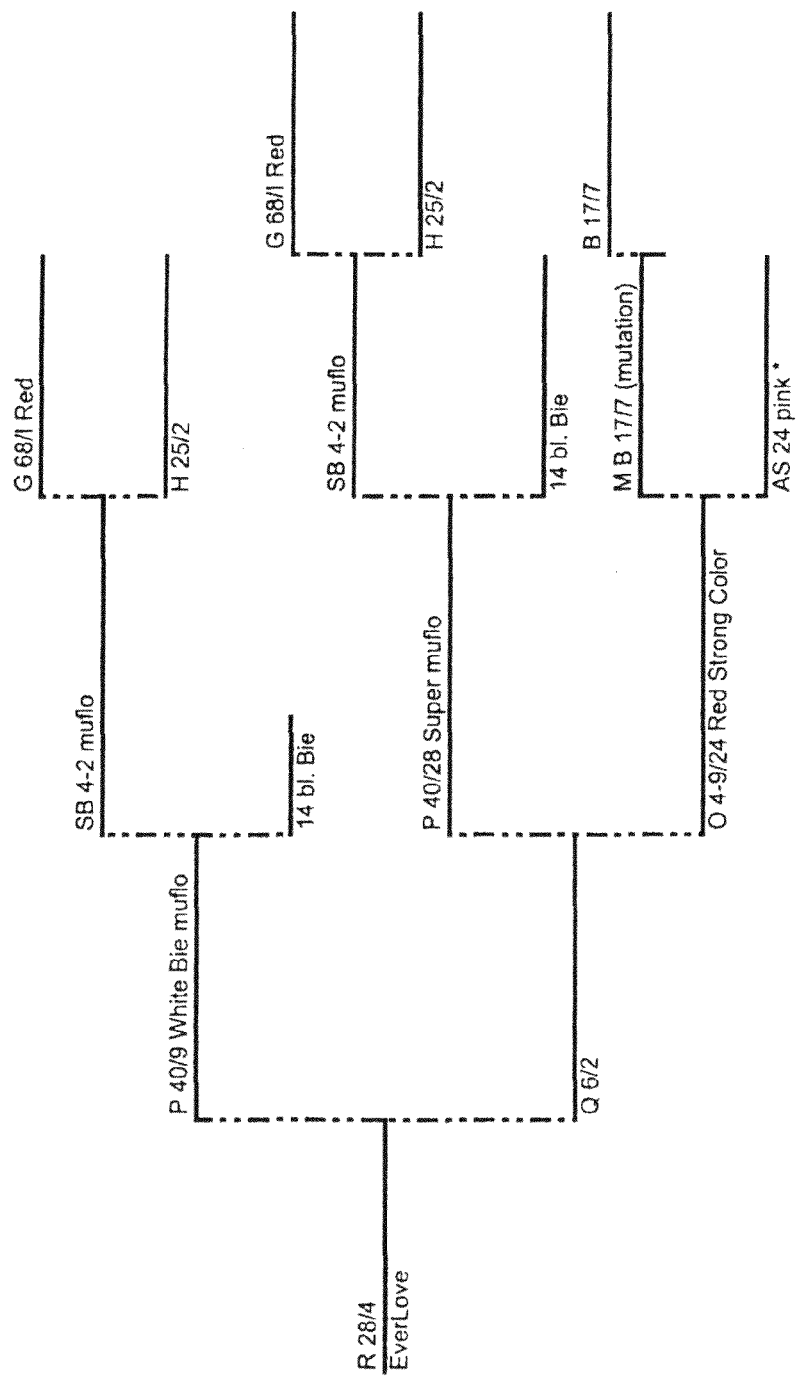
FIG. 5 shows crosses made with 'SB4-2 Muflo' and '14 bl.Bie' to produce multiflorescence cultivar 'EverLove', which is described in U.S. Plant Patent No. 13,186, filed Jan. 17, 2002 and issued May 6, 2003, and incorporated herein by reference.
Figure 6:
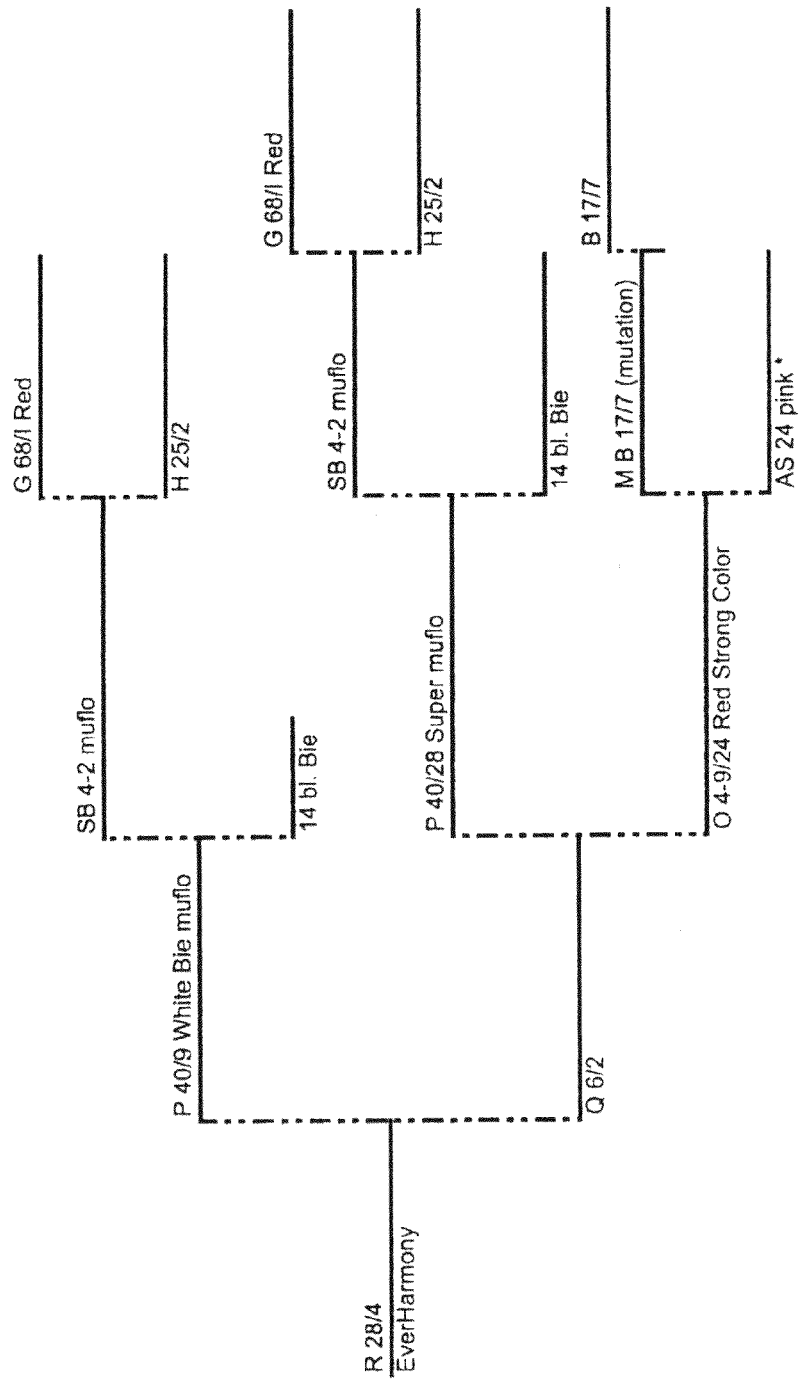
FIG. 6 shows crosses made with 'SB4-2 Muflo' and '14 bl.Bie' to produce multiflorescence cultivar 'EverHarmony', which is described in U.S. Plant Patent No. 13,842, filed Jan. 17, 2002 and issued May 20, 2003, and incorporated herein by reference.

FIGS. 5 and 6 show the breeding work done with 'SB 4-2 Muflo' crossed with non-multiflorescence cultivar designated '14 bl.Bie'. The cultivar '14 bl.Bie' produces flowers that are blue with an outstanding flower bouquet characteristic. This cross proved extremely successful and 106 phenotypes were recorded and designated, 'P 40/1' to 'P 40/106', of which 27 displayed the multiflorescence characteristic, or a success rate of 25% in achieving the desired trait. Among the progeny of this cross, 'P 40/28 super muflo' was selected because of its exceptional floriferous habit and crossed to 'O 4-9/24', a non-multiflorescence selection with flowers having a red star with an exceptionally bright-red color.

The cross yielded 15 recorded phenotypes named 'Q6/1' to 'Q6/15', of which 3 exhibited multiflorescence. 'Q 6/2' was selected, even though it did not exhibit multiflorescence but because it had beautiful flowers with purple-red color with white edge, semi-double, and frilled appearance. 'Q 6/2' was crossed back to a sibling of its mother designated 'P 40/9 muflo', a white flowered compact cultivar with a nice flower bouquet. From this cross, 6 phenotypes were recorded of which 4 exhibited the multiflorescence trait. Two of the selections exhibiting multiflorescence were designated 'EverLove' with a red flowers, and 'EverHarmony' with white and light pink flowers.

In this manner described above, the multiflorescence trait has been successfully fixed in the breeding material so that the multiflorescence trait can be easily and predictably bred into diverse African Violet genetic backgrounds. Multiflorescence has been successfully combined with a large number of desirable African Violet characteristics including different flower colors, leaf colors and growth habit. The different cross breeding methods have transmitted the multiflorescence characteristic approximately 50% of the time in crosses including one parent exhibiting multiflorescence trait and approximately 80% of the time in crosses when both parents exhibit the multiflorescence trait.

It has also been noted, that the number of flower stems per leaf axil increases as the African Violet plant with the multiflorescence trait ages. The older the plant, the more likely the plant is to have three or more flower stems emerging from each leaf axil. The number of blooms per flower stem also increases. The only environmental stress factor that appears to adversely affect the multiflorescence trait is a lack of adequate fertilization. The multiflorescence trait is gradually restored as soon as adequate fertilization resumes.

I claim:

1. An African Violet plant comprising at least one leaf axil that produces at least three flower stems.

2. The African Violet plant of claim 1 wherein the leaf axil produces at least 4 flower stems.

3. The African Violet plant of claim 1 wherein the plant is produced from seeds having ATCC deposit Accession No. PTA-3982.

4. A method of producing an African Violet plant having at least one leaf axil with more than one flower stem and a second desirable trait, the method comprising the steps of crossing, as the male or female parent, a first African Violet plant that has at least one leaf axil with more than one flower stem, with a second African Violet plant having a second desirable trait but only 1 flower stem on any leaf axil, and selecting progeny that have at least one leaf axil with more than one flower stem and the second desirable trait.

5. The method according to claim 4, wherein the second desirable trait is selected from the group consisting of flower color, leaf color, disease resistance, leaf size and growth habit.

6. African Violet seeds produced by the method of claim 4, wherein the seeds produce a plant comprising at least one leaf axil that has more than one flower stem.

7. A method of increasing the number of flower stems per leaf axil in a African Violet plant comprising the steps of crossing a first plant that exhibits the multiflorescence trait with a second plant that exhibits the multiflorescence trait and selecting progeny from the cross that produce more flower stems per leaf axil than either parent.

8. An African Violet plant comprising at least one leaf axil that produces at least two flower stems, wherein the flower stems are united.

9. The African Violet plant of claim 8, wherein the flower stems are united at the base of the axil.

* * * * *